United States Patent
Calasso et al.

(10) Patent No.: US 10,099,008 B2
(45) Date of Patent: Oct. 16, 2018

(54) ROTOR FOR MEDICAL FLOW-REGULATING DEVICES

(71) Applicant: Medirio Sa, Visp (CH)

(72) Inventors: Irio Giuseppe Calasso, Arth (CH); Luca Calasso, Zurich (CH); Matteo De Donatis, Sion (CH)

(73) Assignee: Medirio S.A., Visp (CH)

( * ) Notice: Subject to any disclaimer, the term of this patent is extended or adjusted under 35 U.S.C. 154(b) by 777 days.

(21) Appl. No.: 14/623,269

(22) Filed: Feb. 16, 2015

(65) Prior Publication Data
US 2015/0265766 A1    Sep. 24, 2015

(30) Foreign Application Priority Data

Feb. 20, 2014  (EP) .................................... 14156056

(51) Int. Cl.
| | | |
|---|---|---|
| *A61M 5/168* | (2006.01) | |
| *A61M 5/142* | (2006.01) | |
| A61M 39/22 | (2006.01) | |

(52) U.S. Cl.
CPC ........ *A61M 5/16804* (2013.01); *A61M 5/142* (2013.01); *A61M 5/14248* (2013.01); *A61M 5/16881* (2013.01); A61M 5/14232 (2013.01); A61M 2005/14268 (2013.01); A61M 2039/226 (2013.01); A61M 2205/0272 (2013.01); A61M 2205/103 (2013.01); A61M 2205/8237 (2013.01); A61M 2205/8287 (2013.01); A61M 2207/00 (2013.01); Y10T 29/49826 (2015.01)

(58) Field of Classification Search
CPC ........ A61M 2005/14533; A61M 1/036; A61M 2005/2086; A61M 5/31528; A61M 5/3155–5/31553; A61M 5/31583; A61M 5/31585; A61M 5/31586; F16K 35/16; F16K 31/08
See application file for complete search history.

(56) References Cited

U.S. PATENT DOCUMENTS

| | | | | |
|---|---|---|---|---|
| 4,443,214 A | | 4/1984 | Marion | |
| 4,453,508 A | * | 6/1984 | Groeger | .................. F02B 75/36 123/193.1 |
| 4,562,802 A | * | 1/1986 | Groeger | .................. F02B 75/36 123/200 |
| 5,549,458 A | * | 8/1996 | Chapman | ............ F04B 43/1253 417/360 |
| 5,643,194 A | * | 7/1997 | Negre | .................. A61M 27/006 137/385 |
| 7,686,786 B2 | * | 3/2010 | Moller | .............. A61M 5/14566 604/134 |

(Continued)

*Primary Examiner* — Matthew F Desanto
(74) *Attorney, Agent, or Firm* — Blank Rome LLP

(57) ABSTRACT

A rotor for medical flow-regulating devices is described. The rotor comprises a central body and a margin extending from the central body. The margin comprises at least one actionable section that is movable from a rest position to a stretched position with respect to the central body upon application of a force and is configured to resiliently return to the rest position upon removal of the force. A medical flow-regulating device comprising the rotor is also described. A system comprising the medical flow-regulating device and a hand-held activation device is also described. A method of manufacturing a rotor is also described.

10 Claims, 7 Drawing Sheets

(56) References Cited

U.S. PATENT DOCUMENTS

2005/0090782 A1* 4/2005 Marshall .......... A61M 5/31525
                                                     604/211
2008/0319394 A1* 12/2008 Yodfat .............. A61M 5/14248
                                                     604/154
2012/0245515 A1   9/2012 Calasso et al.

* cited by examiner

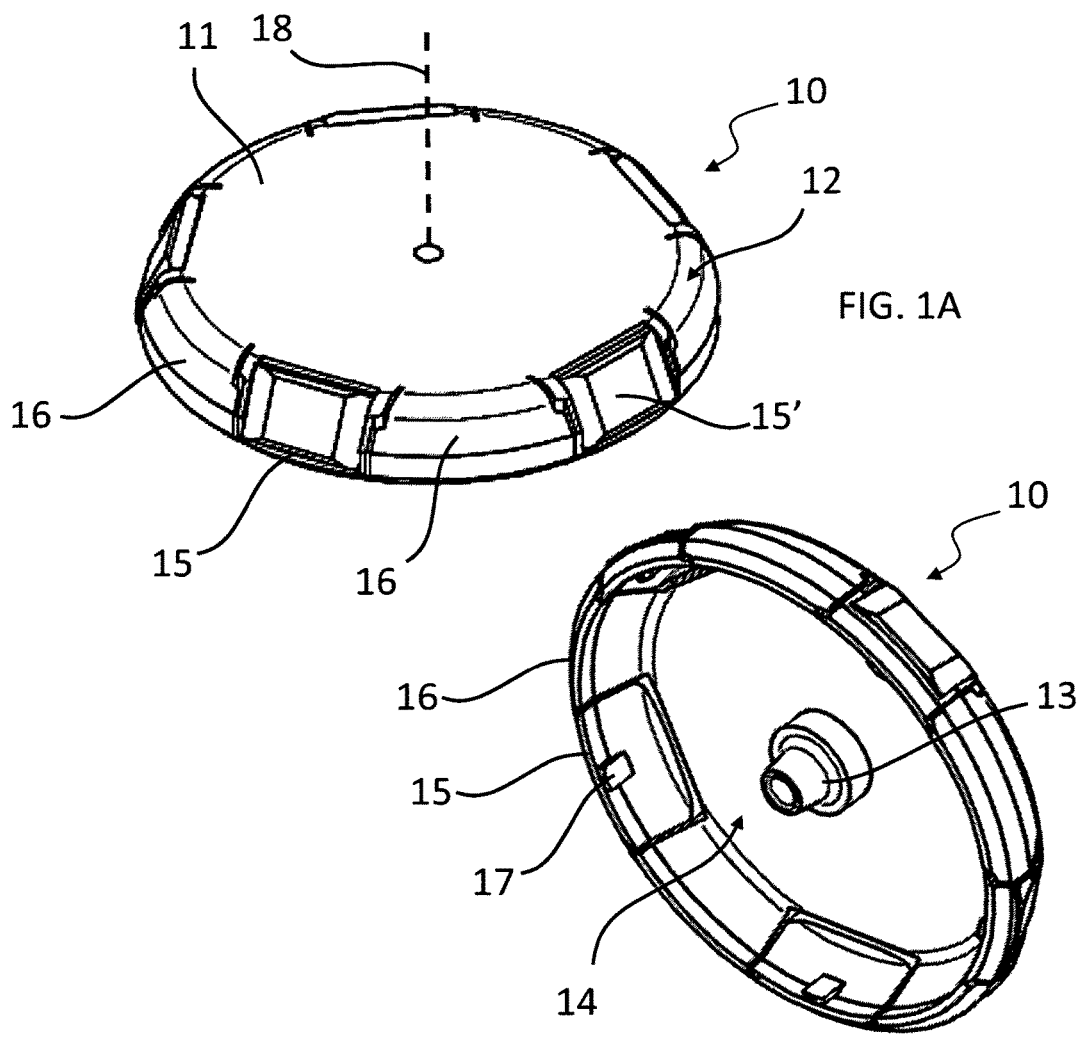
FIG. 1A
FIG. 1B
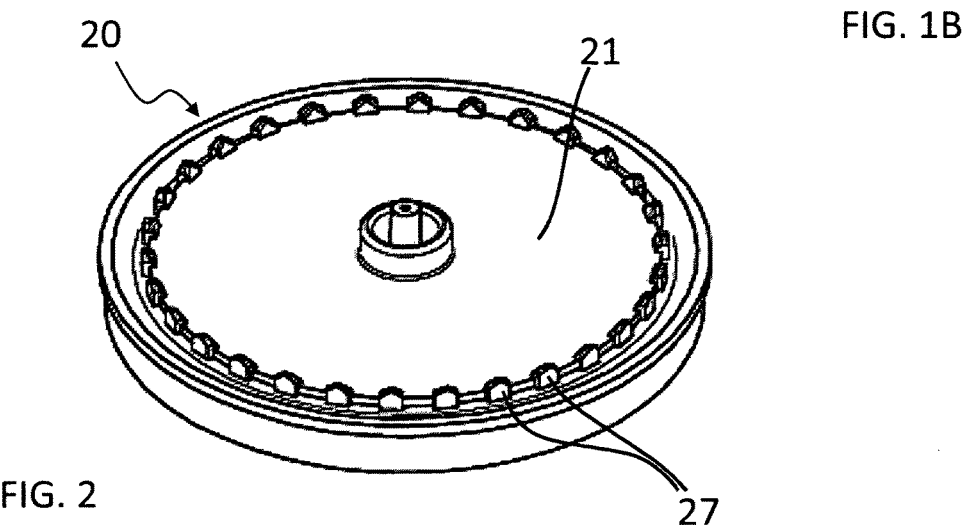
FIG. 2

ROTOR FOR MEDICAL FLOW-REGULATING DEVICES

FIELD OF THE INVENTION

The present invention relates to a rotor configured to operate in connection with a flow regulator of a medical flow-regulating device. The invention also refers to a medical flow-regulating device comprising the rotor and to a system comprising the medical flow-regulating device. The invention also refers to a method of manufacturing a rotor.

BACKGROUND OF THE INVENTION

Some medical conditions require the regular dosage of medicaments. These medicaments are often provided as liquid solutions to be infused, e.g. transdermally. Diabetic patients, for example, may require several infusions of insulin every day. In the attempt to make the life of these patients easier, infusion devices have been developed. The infusion devices known in the art typically comprise a syringe-type pump, and use electro-mechanical pumping to deliver the medicament to the patient through the skin. They typically comprise also all the elements needed for operation and control, e.g. a processor, electric components, a battery, buttons or switches located on the housing of the device, visual feedback via text or graphic screen, etc . . . . These are however expensive, difficult to use and tend to be bulky and uncomfortable. Moreover, they require specialized care, maintenance and cleaning to assure proper functionality and safety for their intended long-term use. Other types of medical devices have been therefore proposed. US2012245515A1 discloses a medical flow-regulating device comprising a medicament reservoir, a pump and a rotor connected to the pump for pumping the medicament from the reservoir when the rotor rotates, the rotor being driven by an external hand-held activation device. An advantage of such a medical flow-regulating device is that it comprises a small number of components and is therefore small and inexpensive. Moreover, it is comfortable, discreet, and easy to use. It is also safe since it further comprises a safe-lock mechanism, which can be unlocked in a specific manner by the hand-held activation device.

It is desirable to further reduce the costs of production of a medical flow-regulating device by further reducing the number of its components and/or by simplifying the design and the construction of its components.

SUMMARY OF THE INVENTION

It is against the above background that the present invention provides certain unobvious advantages and advancements over the prior art.

In particular, a new, simple, inexpensive, light, small and at the same time multifunctional rotor for medical flow-regulating devices is described. The rotor comprises a central body and a margin extending from the central body. The margin comprises at least one actionable section that is movable from a rest position to a stretched position with respect to the central body upon application of a force and is configured to resiliently return to the rest position upon removal of the force. A medical flow-regulating device comprising the rotor is also described. A system comprising the medical flow-regulating device and a hand-held activation device is also described. A method of manufacturing a rotor is also described.

The same type of rotor may be used also in any type of medical flow-regulating device, including implantable medical flow-regulating devices, as long as a rotatable mechanism configured to regulate a fluid flow, e.g. a pump or a valve but not limited thereto, connected or connectable to a rotor is employed.

These and other features and advantages will be more fully understood from the following detailed description taken together with the accompanying claims. It is noted that the scope of the claims is defined by the recitations therein and not by the specific discussion of features and advantages set forth in the description.

BRIEF DESCRIPTION OF THE DRAWINGS

FIG. 1A shows an example of a rotor for medical flow-regulating devices and in particular a perspective view of the rotor from the upper side.

FIG. 1B shows a perspective view of the same rotor of FIG. 1A from the bottom side.

FIG. 2 shows an example of blocking element functionally coupable to a rotor such as the rotor of FIG. 1a and FIG. 1B.

FIG. 6A is a perspective view of a first layer from the upper side.

FIG. 6B is a perspective view of a second layer from the upper side.

FIG. 6C is a perspective view of the second layer from the bottom side.

FIG. 6D is a perspective view of the first layer from the bottom side.

DETAILED DESCRIPTION

Figure 3:
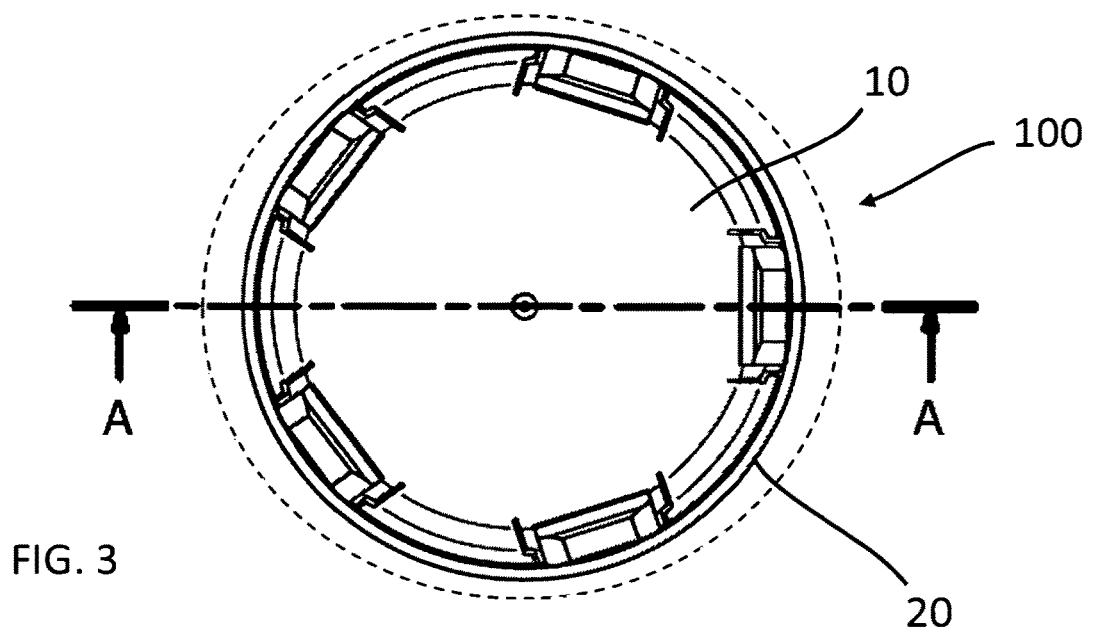
FIG. 3 is a schematic top view of a medical flow-regulating device comprising the rotor of FIG. 1a and FIG. 1B and the blocking element of FIG. 2.

A rotor for medical flow-regulating devices is described.

A "medical flow-regulating device" is a device, which is configured to be placed in contact with a patient and to perform medical treatment by regulating the flow of a fluid in the patient's body or into the patient's body or out of the patient's body. "Regulating" means changing by e.g. increasing, decreasing, starting, interrupting or resuming the flow of a fluid. This may comprise pumping a fluid either continuously or at intervals, either at constant or variable flow rate.

"In contact" thus means either in dermal contact with the patient, e.g. removably fixed, e.g. by an adhesive layer, to the skin of the patient, or more generally in body contact, comprising the inside of the body, such as fixed at least in part in a cavity of the body or implanted inside the body.

An example of fluid is a medicament for treating a medical condition, e.g. insulin to treat a diabetic condition, a pain-treating drug to treat the symptoms of a chronic disease, an anti-coagulation drug to reduce the risk of thrombosis, e.g. after surgery, a hormone to treat or change other medical conditions, etc . . . The fluid may be otherwise a body fluid or an external fluid passing through a body fluidic conduit.

According to certain embodiments the medical flow-regulating device is a medical infusion device configured to deliver trans-dermally or intravenously multiple doses of a fluidic medicament to a patient without the need of multiple injections. A typical example of patient is a diabetic patient requiring frequent doses of insulin, e.g. in correspondence to each meal. According to one embodiment, the medical flow-regulating device is an implantable device or a device partly in the body and partly out of the body, e.g. a catheter. The medical flow-regulating device may be embodied as a valve device configured to enable/disable fluid flow or vary the flow rate of a fluid, e.g. a body fluid, or as a continuous infusion device, configured to deliver a continuous flow of a medicament with a flow rate, which may be changed over time. Medical treatment may otherwise result from regulation of the flow of a fluid from outside the body into the body or from inside the body to the outside of the body, e.g. to temporarily interrupt the flow of a fluid, e.g. urine in incontinent patients, or to drain off excess of a fluid produced by the body, e.g. interstitial fluid in edematous patients, or from regulation of the flow of a body fluid within the body, i.e. from one part of the body to another, e.g. cerebrospinal fluid in order to decrease intracranial pressure, or from regulation of the passage of an external fluid through the body, e.g. food or drinks through the digestive duct, e.g. in order to regulate appetite and treat obesity.

A "rotor" is a rotatable medical flow-regulating device component, which allows the medical flow-regulating device to regulate the flow of a fluid upon rotation. The term "rotation" is used here generically to indicate any number of revolutions or fractions of a revolution without limit of time. Also, rotation may occur in opposite or alternate directions, with constant motion, accelerated motion, or pulse, or combinations thereof.

In particular, the rotor comprises a central body and a margin extending from the central body. The rotor is generally designed to occupy the least space possible within the medical flow-regulating device and using the least number of components and the least amount of material, in order to minimize size, weight and costs. The central body can have in theory any shape as long as it can be coupled to a flow-regulating mechanism, e.g. a pump or a valve but not limited thereto, such as to transfer rotational force to it upon rotation. According to certain embodiments the central body can have a disc, plate, rod, rim, wheel, polygonal, star shape or the like. The margin is an extension or protrusion of the central body, located at the periphery of the central body, integrally formed with the body or attached thereto, or in part integrally formed with the central body and in part attached thereto, and which can extend in any direction for a pre-defined distance, from any side of the central body, as long as it can fit in the medical flow-regulating device and exercise its intended function as below described. In particular, the margin comprises at least one actionable section, which is movable from a rest position to a stretched position with respect to the central body upon application of a force and is configured to resiliently return to the rest position upon removal of the force. The actionable section is therefore to a certain extent flexible with respect to the central body, i.e. at least in part movable in the direction of the applied force or with a movable component in the direction of the applied force. The term "actionable" thus means reversibly stretchable upon application of a push or pull force in a certain direction.

According to certain embodiments the rotor further comprises at least one reference section providing a stop for the at least one actionable section in the stretched position. The reference section has therefore a higher degree of rigidity compared to the actionable section, at least in the direction of the force applied to the actionable section, such as to remain stationary with respect to the rotor and act as a stop for the actionable section, upon application of a force sufficient to stretch the actionable section. The reference section can be part of the central body or of the margin or both.

According to certain embodiments, the margin comprises at least one actionable section adjacent to at least one reference section and/or alternating reference and actionable sections adjacent to each other. The term "adjacent" comprises next to each other, side by side, or superimposed to each other, e.g. one above the other or partially overlapping each other, as long as the at least one reference section can act as stop for the at least one actionable section in the stretched position.

According to certain embodiments, the at least one actionable section is made of or comprises a magnetic or ferromagnetic material and is movable towards a stretched position upon application of a magnetic force, which can be attractive or repulsive.

According to certain embodiments, the rotor is manufactured as one piece made of or comprising a ferromagnetic or magnetic material.

According to certain embodiments, the central body and/or the at least one reference section is made of or comprises a non-magnetic material or material with negligible magnetic properties and/or a non-ferromagnetic material. This includes for example plastic materials in general, non-ferromagnetic metals, e.g. aluminum, ceramics, composite materials, alloys or the like.

According to certain embodiments, the rotor comprises a first layer, preferably made of a non-magnetic material or material with negligible magnetic properties and/or a non-ferromagnetic material, including for example plastic materials in general, non-ferromagnetic metals, e.g. aluminum, ceramics, composite materials, alloys or the like, and a second layer of ferromagnetic or magnetic material, the at least one reference section being integral or being attached to the first layer and the at least one actionable section being integral or being attached to the second layer.

According to certain embodiments, the medical flow-regulating device comprises at least one blocking element engageable with the at least one actionable section in the rest position.

In particular, the at least one actionable section is engageable with the blocking element, when it is in the rest position, or when it returns to the rest position after having being stretched. When the at least one actionable section is in the rest position, the blocking element therefore locks the rotor preventing the rotor to rotate. The at least one actionable section is disengageable from the blocking element by moving it from the rest position to the stretched position, thereby unlocking the rotor and allowing the rotor to rotate.

The function of the at least one reference section is to prevent that the actionable section is stretched further beyond the stop position, which may otherwise result in undesired contact of the actionable section with other parts of the medical flow-regulating device, when the rotor is unlocked, thus possibly causing friction and/or impeding rotation. The extent of the stretching can be thus reliably and reproducibly controlled allowing the rotor to rotate freely in the stretched position. Also the extent of stretching can be small, i.e. sufficient to disengage from the blocking element, thereby maintaining the overall size of the rotor and the medical flow-regulating device small.

According to certain embodiments, the medical flow-regulating device further comprises a pump or a valve directly or indirectly connected or connectable to the rotor for regulating a fluid flow when the rotor is rotated.

A system comprising a medical flow-regulating device and a hand-held activation device separate from the medical flow-regulating device is also described. The activation device comprises an unlocking/drive unit. In absence of the activation device, the at least one actionable section is in the rest position and is engaged with the blocking element. The rotor is thus locked and prevented to rotate. The rotor is unlockable and rotatable by temporarily docking the activation device to the medical flow-regulating device in an energy transfer position, which enables the unlocking/drive unit to transfer the force required to move the at least one actionable section to the stretched position thereby unlocking the rotor and to transfer a rotational force to the rotor required for rotating the unlocked rotor. The rotor is again lockable by removing the activation device from the energy-transfer position, thus removing the source of force, which keeps the at least one actionable section in the stretched position, and allowing the at least one actionable section to return to the rest position in engagement with the blocking element.

A method of manufacturing a rotor according to certain embodiments is also disclosed. The method comprises manufacturing a layer of ferromagnetic or magnetic material comprising a central body and a margin, the margin comprising at least one actionable section. In particular the layer may comprise a central body, shaped e.g. as a disk or as ring, wherein the at least one actionable section extends from the central body radially outwards. It may be advantageous to manufacture the layer out of a flat sheet of material with magnetic or ferromagnetic properties, e.g. by laser cutting, milling, etching or any other conventional technique. According to some embodiments, the layer may be magnetized in a subsequent step after having been manufactured. The layer may advantageously comprise parts, e.g. points or lines of reduced thickness or width, perforated lines or the like, for increasing flexibility with respect to the central body. According to an embodiment, the method comprises bending the at least one actionable section with respect to the central body. In particular, the method may comprise folding the at least one actionable section on itself to form a thickened actionable section. The layer may advantageously comprise folding points or lines, e.g. parts of reduced thickness or width, perforated lines or the like, for facilitating and/or guiding the folding and/or bending in correspondence to these parts. Increasing the thickness of the actionable section by folding parts of the layer on itself can have the function of increasing the sensitivity to an external magnetic force.

According to certain embodiments, the method further comprises manufacturing a layer of non-magnetic or non-ferromagnetic material comprising a central body directly or indirectly connectable to a flow-regulating mechanism and coupling the layer of non-magnetic or non-ferromagnetic material with the layer of magnetic or ferromagnetic material. The layer of non-magnetic or non-ferromagnetic material may be formed using conventional manufacturing processes, e.g. by injection molding.

According to certain embodiments, manufacturing the layer of non-magnetic or non-ferromagnetic material comprises forming a margin with at least one reference section for the at east one actionable section of the magnetic or ferromagnetic material. The rotor is thus formed by the combination of the layer of magnetic or ferromagnetic material having at least one actionable section and the layer of non-magnetic or non-ferromagnetic material having at least one element, e.g. a shaft, gear, hole or the like to be connected directly or indirectly to a flow-regulating mechanism and having at least one reference section to control the movement of the at least one actionable section in the stretched position.

More in detail the present invention is explained with reference to the accompanying drawings representing schematically exemplary embodiments.

FIG. 1A shows a first example of rotor 10 and in particular a perspective view of the rotor 10 from the upper side whereas FIG. 1B shows a perspective view of the same rotor 10 from the bottom side. In particular, the rotor 10 comprises a central body 11 and a margin 12 extending from the central body 11. The central body 11 has a circular planar disc shape and can be coupled to a flow-regulating mechanism (not shown), e.g. a pump or a valve, via a shaft 13, arranged at the center of the body 11. The rotor 10 has an axis of symmetry 18 passing through the center of the central body 11 and through the shaft 13. The rotor 10 is rotatable about the axis 18 such as to transfer rotational force to the shaft 13 and to the flow-regulating mechanism upon rotation. The margin 12 is in part integrally formed with the central body 11 and extends along the circumference of the central body 11 out of the plane of the central body 11 such as to form a recess 14 at one side of the central body 11 where the shaft 13 is located. The recess 14 may be advantageously used to accommodate for example the flow-regulating mechanism, e.g. a peristaltic pump, e.g. connected via a gear coupling to the shaft 13.

The margin 12 comprises a plurality of actionable sections 15 alternated to a plurality of reference sections 16, adjacent to each other. In particular, each reference section 16 slightly overlaps at two sides two adjacent actionable sections 15, with the actionable section being more biased towards the center of the rotor 10 at angle with respect to the reference sections 16. The actionable sections 15 in part and the reference sections 16 are integrally formed with the margin 12 and with the central body 11 out of a single piece of plastic material, e.g. injection molded. The actionable sections 15 further comprise ferromagnetic elements 15' attached to the outer surface. The plastic component of the actionable sections 15 is at least partially thinner than the reference sections 16, so that the thickness of the plastic component of an actionable section 15 and of the ferromagnetic material attached thereto is about the same or comparable to the thickness of a reference section 16. The actionable sections 15 have also a line of connection 15" to the central body 11 which is thinner compared to the line of connection 16' of the reference sections 16, so that the actionable sections 15 can be stretched about these lines of connection 15" upon application of an attractive magnetic force external to the rotor 10 and acting on the ferromagnetic elements 15', e.g. in a direction orthogonal to or at an angle with respect to the axis of symmetry 18 of the rotor 10. In particular, each actionable section 15 is movable from a rest position, biased towards the center of the rotor 10, to a stretched position, biased towards the outside of the rotor 10 away from the center of the central body 11 upon application of a magnetic force. The extent of stretching is determined by the position of the adjacent reference sections 16 acting as a stop for the actionable sections 15, where the reference sections 16 have a higher degree of rigidity compared to the actionable sections 15, in the direction of the force applied to the actionable section 15, and remain stationary with respect to the central body 11, upon application of a force sufficient to stretch the actionable sections 15. The actionable sections 15 are resiliently configured to return to the rest position upon removal of the magnetic force. This mechanism is better understandable in connection to FIG. 5. The actionable sections 15 further comprise a protrusion 17 located on the inner surface towards the center of the rotor 10.

FIG. 2 shows an example of blocking element 20 functionally coupable with the rotor 10. The blocking element 20 has also a central body 21 with a planar circular disc shape, having a diameter similar to the diameter of the central body 11 of the rotor 10 and forming a closed space between the rotor 10 and the blocking element 20 when they are functionally coupled. The blocking element 20 comprises teeth 27 arranged at regular intervals along the circumferential periphery of the central body 21 so that the protrusions 17 of the actionable sections 15 are insertable between the teeth 27, when the actionable sections 15 are in the rest positions, regardless of the angular position of the rotor 10. In particular, rotation of the rotor 10 is prevented by the blocking element 20 unless in presence of a sufficient symmetrical magnetic force acting at the same time radially outwards on all actionable sections 15 of the rotor 10.

FIG. 3 is a schematic top view of a medical flow-regulating device 100 comprising the rotor 10 of FIG. 1 and the blocking element 20 of FIG. 2.

Figure 4:
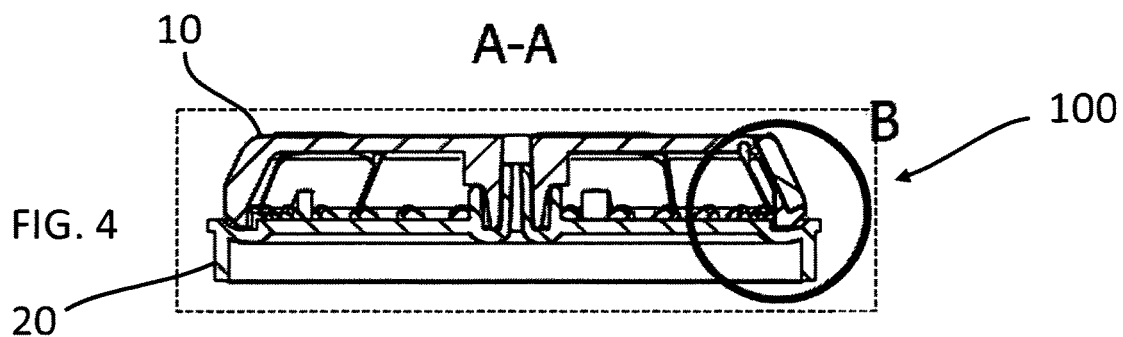
FIG. 4 is a cross section of the medical flow-regulating device of FIG. 3 through line A-A.

FIG. 4 is a cross section of the medical flow-regulating device 100 of FIG. 3 through line A-A. Other parts of the medical flow-regulating device 100 have been removed for clarity to better show the relationship between the rotor 10 and the blocking element 20. The medical flow-regulating device 100 comprises otherwise at least a flow-regulating mechanism, e.g. a pump or a valve, which can be conveniently arranged in the space between the rotor 10 and the blocking element 20. The medical flow-regulating device 100 may further comprise a medicament reservoir, e.g. arranged below the blocking element 20, such as e.g. disclosed in US2013338592, and not further elucidated here.

Figures 5A, 5B:
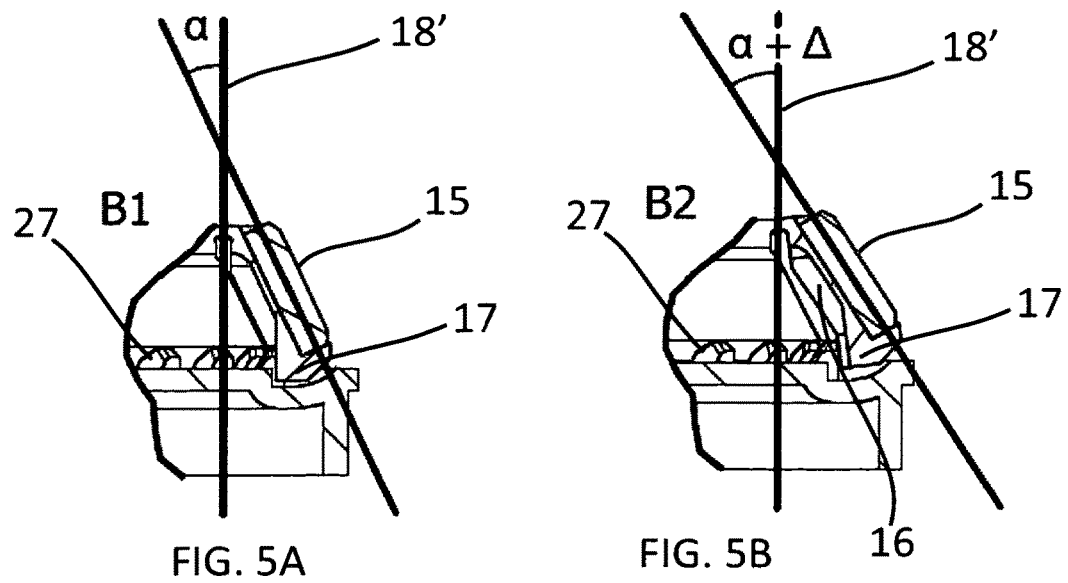
FIG. 5A is a magnification of detail B of FIG. 3 and in particular shows an actionable section in a rest position.
FIG. 5B shows the same actionable section of FIG. 5A in a stretched position.

FIG. 5A is a magnification of detail B of FIG. 3 and in particular it shows an actionable section 15 of the rotor 10 in a rest position. In this rest position the actionable section 15 is at an angle α with respect to an axis 18' orthogonal to the plane of the central body 11. Also, the protrusion 17 is engaged between two teeth 27 of the blocking element 20, thereby preventing the rotor 10 to rotate. FIG. 5B shows the same actionable section 15 in a stretched position. In this stretched position the actionable section 15 is at an angle α+Δ, i.e. at a larger angle, with respect to an axis 18' orthogonal to the plane of the central body 11, where Δ is the degree of stretching, and where Δ is determined by the stop provided by the reference section 16. In this stretched position, the protrusion 17 is disengaged from the teeth 27 of the blocking element 20, thereby enabling rotation of the rotor 10.

Figure 6A:
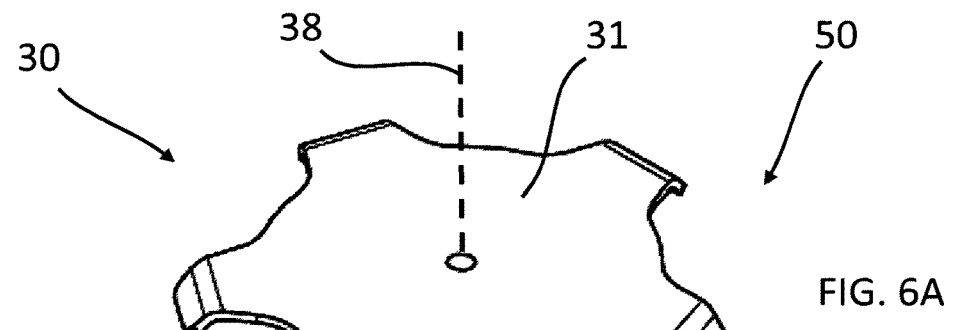
FIGS. 6A-6B when seen together represent an exploded view of a different example of rotor comprising two layers.
Figure 6B:
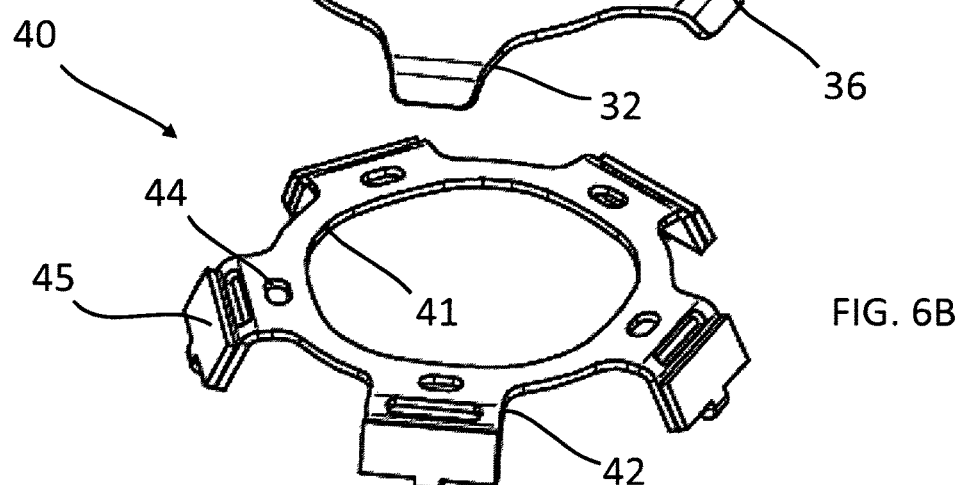
Figure 6C:
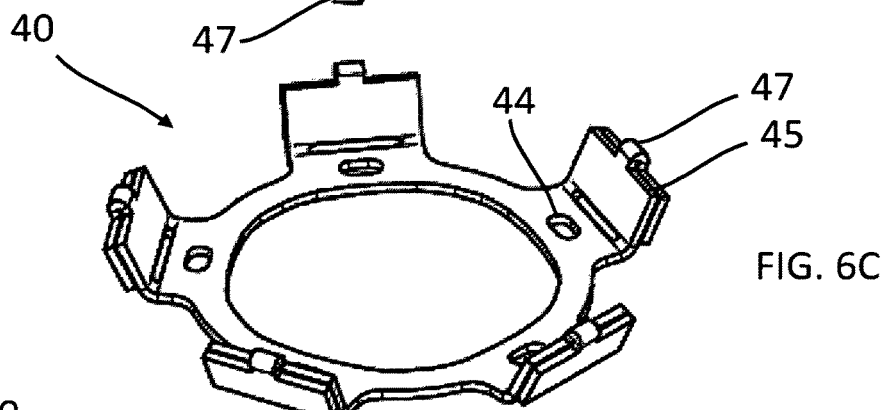
FIGS. 6C-6D when seen together represent an exploded view of the same rotor of FIG. 6a-6b upside down.
Figure 6D:
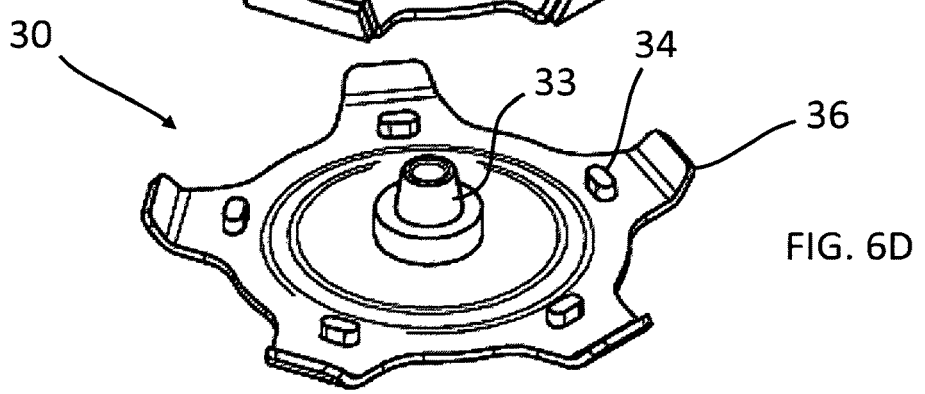

FIGS. 6A-6B together are an exploded view of a different example of rotor 50 comprising a first layer 30 of plastic material and a second layer 40 of ferromagnetic material. In particular, FIG. 6A is a perspective view of the first layer 30 from the upper side, FIG. 6B is a perspective view of the second layer 40 from the upper side. FIG. 6C is a perspective view of the second layer 40 from the bottom side. FIG. 6D is a perspective view of the first layer 30 from the bottom side. The layer of plastic material 30 is made of one piece comprising a disc shaped central body 31 and a margin 32, the margin 32 comprising bent portions 36 extending from the central body 31 and acting as reference sections. The layer of ferromagnetic material 40 is made of one piece comprising a ring shaped central body 41 and a margin 42. The margin 42 comprises a plurality of bent portions 45 folded on themselves, which act as actionable sections and correspond in number to the number of the reference sections 36. The central body 31 of the first layer 30 comprises a shaft 33, arranged at the center of the central body 31, that can be coupled to a flow-regulating mechanism (not shown), e.g. a pump or a valve. The first layer 30 has an axis of symmetry 38 passing through the center of the central body 31 and through the shaft 33. The first layer 30 is rotatable about the axis 38 such as to transfer rotational force to the shaft 33 and to the flow-regulating mechanism upon rotation. The first layer 30 further comprises pins 34 protruding from the lower face of the central body 31 dimensioned to fit in respective holes 44 of the central body 41 of the second layer 40. The first layer 30 and the second layer 40 can be thus connected to each other via the pins 34 and holes 44 respectively such to form one functional rotor 50 rotatable as one unit about the axis 38. It should be clear that this is only one example of connecting the two layers 30, 40 and that other alternative methods or combinations are possible, including the use of adhesive, welding, bonding techniques or the like. The layer of ferromagnetic material 40 further comprises protrusions 47 formed in correspondence to folded portions of the actionable sections 45 engageable with the teeth 27 of a blocking element 20 such as that of FIG. 2. Folding the actionable sections 45 on themselves has thus the double function of increasing the thickness of the ferromagnetic material for increased sensitivity to an external attractive magnetic force and also to create a protrusion 47 engageable with a blocking element 20 in absence of an external magnetic force.

According to an embodiment the layer of ferromagnetic material 40 can be used as a rotor without the layer of plastic material 30. The rotor 40 may be e.g. directly coupled with the central body 41 to a flow-regulating mechanism (not shown), e.g. via the holes 44.

Figure 7:
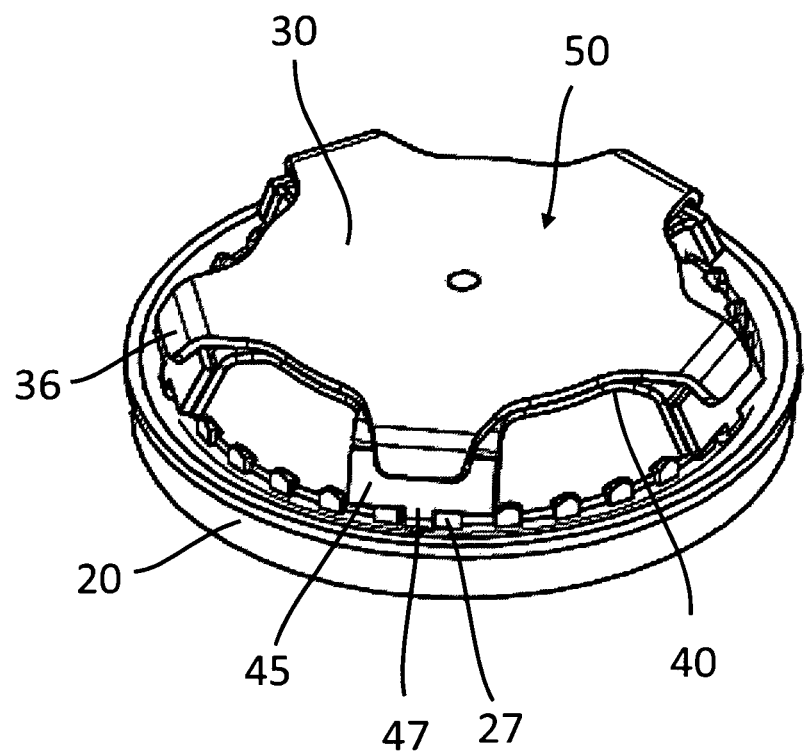
FIG. 7 is a perspective view of the rotor of FIGS. 6A-6D functionally coupled to the blocking element of FIG. 2.

FIG. 7 is a perspective view of the rotor 50 of FIGS. 6A-6D functionally coupled to the blocking element 20 of FIG. 2. In particular, when the first layer 30 is connected to the second layer 40 to form the rotor 50, the reference sections 36 of the first layer 30 are arranged above the actionable sections 45 of the second layer 40, thereby providing a stop for the respective actionable sections 45 when they are stretched outwards and enabling the rotor 50 to rotate. When instead the actionable sections 45 are in the rest position, they are engaged with the blocking element 20 and in particular with the teeth 27 of the blocking element 20 via the protrusions 47, thereby preventing the rotor 50 to rotate.

Figure 8:
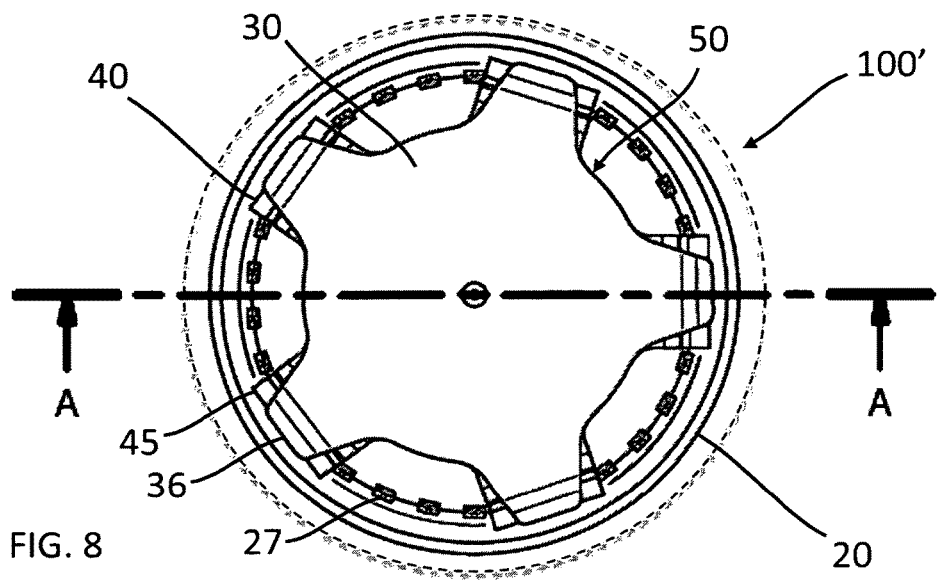
FIG. 8 is a schematic top view of a medical flow-regulating device comprising the rotor of FIG. 6 and the blocking element of FIG. 2 functionally coupled as in FIG. 7.

FIG. 8 is a schematic top view of a medical flow-regulating device 100' comprising the rotor 50 of FIGS. 6A-6B and the blocking element 20 of FIG. 2 functionally coupled to each other as in FIG. 7. The only difference with respect to the medical flow-regulating device 100 of FIG. 3 is in the design of the rotor 50 compared to rotor 10. According to another embodiment the medical flow-regulating devices 100' comprises a rotor of magnetic or ferromagnetic material 40 without the layer of plastic material 30.

Figure 9:
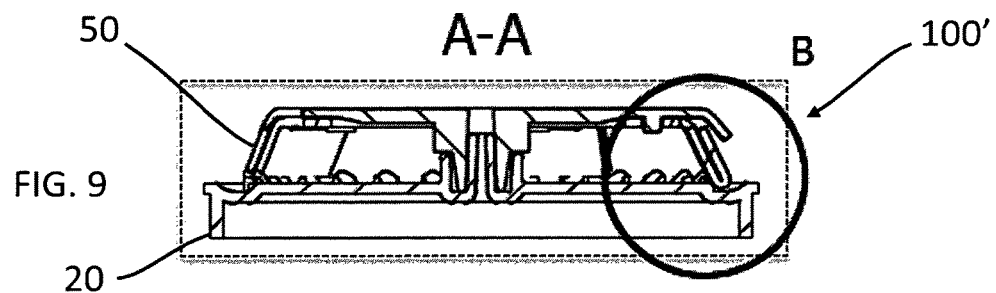
FIG. 9 is cross section of the medical flow-regulating device of FIG. 8 through line A-A.

FIG. 9 is a cross section of the medical flow-regulating device 100' of FIG. 8 through line A-A.

Figure 10A:
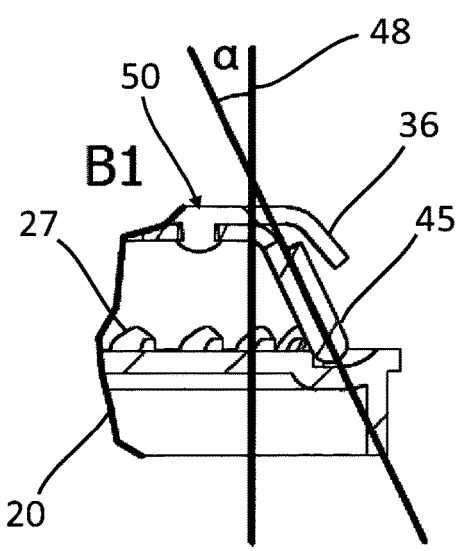
FIG. 10A is a magnification of detail B of FIG. 9 and shows an actionable section in a rest position.
Figure 10B:
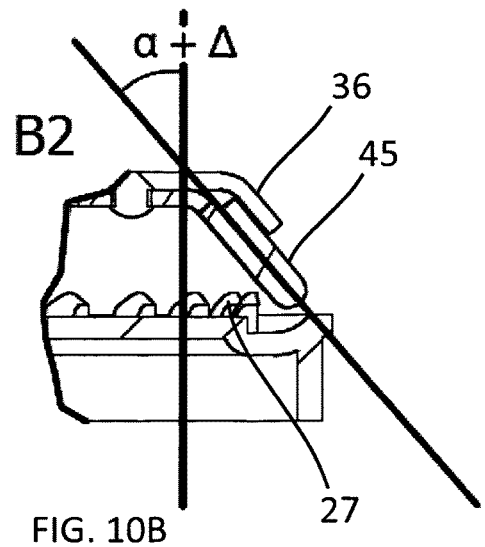
FIG. 10B shows the same actionable section of FIG. 10A in a stretched position.

FIG. 10A is a magnification of detail B of FIG. 9 and in particular it shows an actionable section 45 in a rest position. In this rest position the actionable section 45 is at an angle a with respect to an axis 48 orthogonal to the plane of the central body 41. Also, the protrusion 47 is engaged between two teeth 27 of the blocking element 20, thereby preventing the rotor 50 to rotate. FIG. 10B shows the same actionable section 45 in a stretched position. In this stretched position the actionable section 45 is at an angle $\alpha+\Delta$, i.e. at a larger angle, with respect to an axis 48 orthogonal to the plane of the central body 41, where $\Delta$ is the degree of stretching and where $\Delta$ is determined by the stop provided by the reference section 36. In this stretched position, the protrusion 47 is disengaged from the teeth 27 of the blocking element 20, thereby enabling rotation of the rotor 50.

Figure 11:
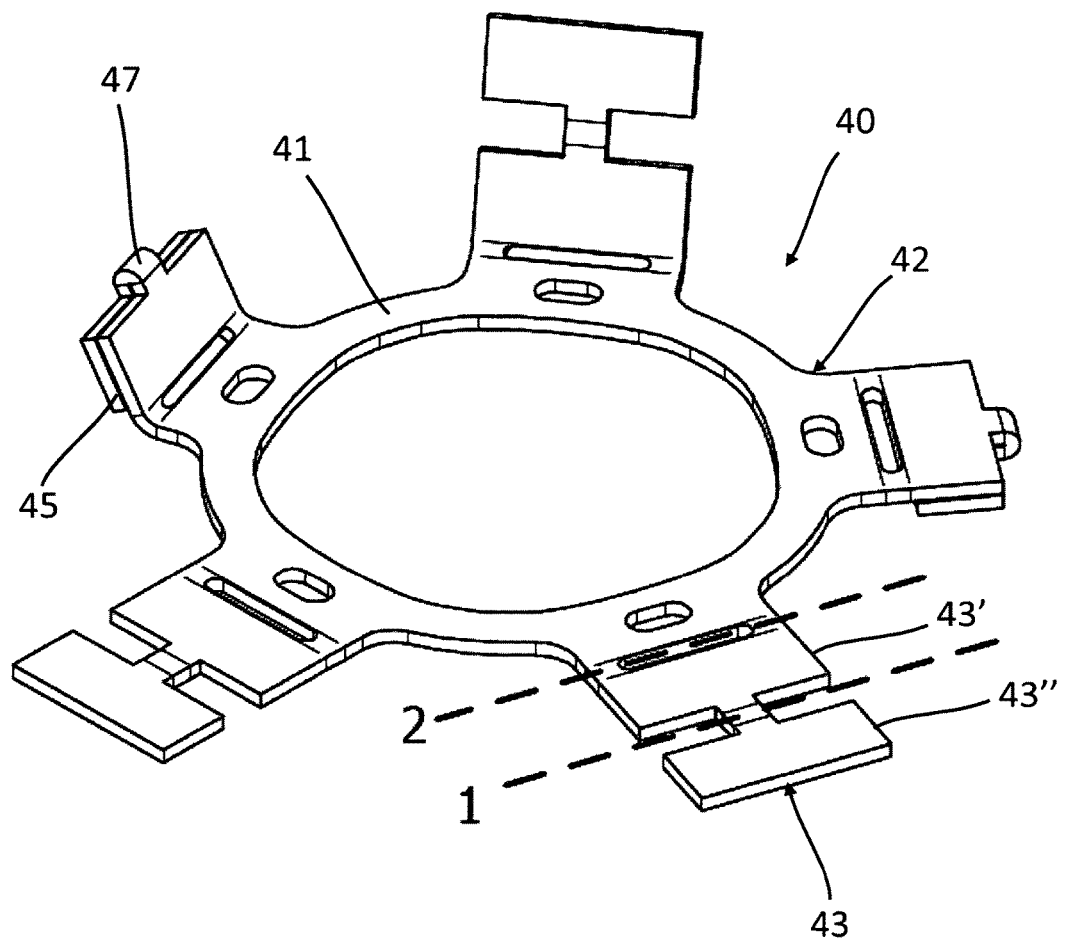
FIG. 11 shows a method of manufacturing a rotor.

FIG. 11 refers to a method of manufacturing a rotor 40 or a layer of magnetic or ferromagnetic material 40 for a multilayer rotor such as the rotor 50 of FIGS. 6A-6D. The method comprises starting from a flat sheet of e.g. a ferromagnetic material, e.g. iron, and cutting out parts to form a central body 41, shaped in this case as a ring, and a margin 42, where the margin comprises a plurality of foldable sections 43 symmetrically extending radially outwards from the ring shaped central body 41. The foldable sections 43 or part of them may act according to certain embodiments as actionable sections 45 without further folding and bending. Each of the foldable sections comprises otherwise two parallel folding lines 1, 2. The first folding line 1 is located radially more outwards and consists of a portion of the layer 40 having reduced width compared to the width of the foldable section 43 and dividing the foldable section 43 in two halves 43', 43" as a hinge in the middle between the two halves 43', 43". The second folding line 2 is located at the border with the central body 41, and comprises a slit in the middle leaving two hinges on either side of the foldable section 43. The method then comprises folding the foldable sections 43 about the hinges of the folding lines 1 in order to fold the foldable sections 43 on themselves, i.e. by bringing the outer halves 43" of the foldable sections 43 on the respective inner halves 43' to form a thickened actionable section 45. The method also comprises bending the actionable sections 45 about the folding lines 2 in order to define the desired angle with respect to the central body 41 in the rest position. The hinges 1, after folding, also act as protrusion 47 engageable with a blocking element 20.

The method further comprises manufacturing a layer of non-magnetic or non-ferromagnetic material, e.g. a plastic material 30 comprising a central body 31 connectable to a flow-regulating mechanism and coupling the layer of plastic material 30 with the layer of ferromagnetic material 40, such as in FIG. 6A-6D. Manufacturing the layer of plastic material 30 comprises forming a margin 32 with reference sections 36 for the actionable sections 45 of the layer of ferromagnetic material 40. The rotor 50 is thus formed by the combination of the layer of ferromagnetic material 40 having a plurality of actionable sections 45 and the layer of plastic material 30 having a corresponding number of reference sections 36 and a shaft or the like to be connected to a flow-regulating mechanism.

Figure 12:
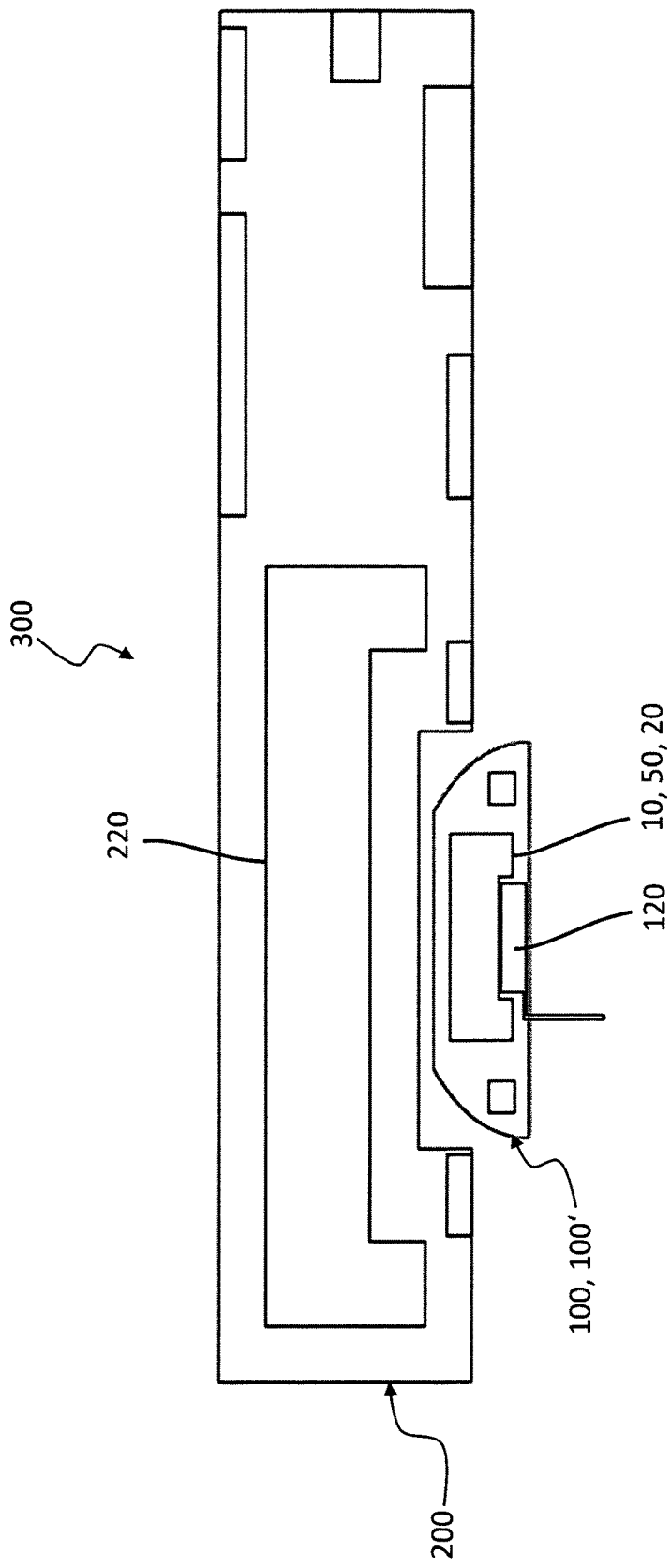
FIG. 12 shows schematically a system comprising a medical flow-regulating device and a hand-held activation device.

FIG. 12 shows schematically a system 300 comprising a medical flow-regulating device 100, 100' and a hand-held activation device 200 in an energy-transfer position. The medical flow-regulating device 100, 100' comprises a flow-regulating mechanism 120 coupled to the rotor 10, 40, 50, and the rotor 10, 40, 50 is coupled to the blocking element 20 (not further detailed in FIG. 12). The hand-held activation device 200 is separate from the medical flow-regulating device 100, 100'. The activation device 200 comprises an unlocking/drive unit 220. The unlocking/drive unit 220 comprises a magnetic field source, capable of generating a magnetic force acting at the same time radially outwards and symmetrically on all actionable sections 15, 45 of the rotor 10, 40, 50. In absence of the activation device 200, i.e. when the hand-held activation device 200 and the medical flow-regulating device 100, 100' are not in the energy transfer position, the actionable sections 15, 45 are in the rest position and are engaged with the blocking element 20. The rotor 10, 50 is thus locked and prevented to rotate. The rotor 10, 40, 50 is unlockable and rotatable by temporarily docking the activation device 200 to the medical flow-regulating device 100, 100' in an energy transfer position, which enables the unlocking/drive unit 220 to transfer the force required to move the actionable sections 15, 45 to the stretched positions thereby unlocking the rotor 10, 40, 50 and to transfer a rotational force to the unlocked rotor 10, 40, 50 required for rotating the unlocked rotor 10, 40, 50. Rotation of the rotor 10, 40, 50 results in transfer of rotation force from the rotor to the flow-regulating mechanism 120 and thereby in medical treatment. The unlocking/drive unit 220 has thus the double function of unlocking the rotor 10, 40, 50 and driving the rotor 10, 40, 50 after unlocking it. The rotor 10, 40, 50 is again lockable by removing the activation device 200 from the energy-transfer position, thus removing the source of force, which keeps the actionable sections 15, 45 in the stretched positions, and allowing the actionable sections 15, 45 to return to the rest positions in engagement with the blocking element 20. The hand-held activation device may have other functions, e.g. functions of control, feedback and interface functions, such as e.g. disclosed in US2013181538 and not further elucidated here.

Of course numerous variations of the described embodiments are possible without departing from the scope of the claimed invention. It is also noted that terms like "preferably" and "typically" or "typical" or "advantageous" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

The invention claimed is:

1. A rotor for a medical flow-regulating device, the rotor comprising:
    a central body and a margin extending from the central body, the margin comprising at least one actionable section which is reversibly flexible upon application of a force allowing the at least one actionable section to move from a rest position to a stretched position with respect to the central body and to return to the rest position upon removal of said force, wherein the at least one actionable section comprises magnetic or ferromagnetic material, wherein the rotor is configured so that said force when applied by a separate hand-held activation device in an energy transfer position moves the at least one actionable section from the rest position to the stretched position thereby unlocking the rotor, and wherein the rotor is lockable by removing the force generated by the activation device.

2. Rotor according to claim 1 wherein the rotor further comprises at least one reference section providing a stop for the at least one actionable section in the stretched position.

3. Rotor according to claim 2 wherein the central body and/or the at least one reference section is made of or comprises a non-magnetic material or material with negligible magnetic properties and/or a non-ferromagnetic material.

4. Rotor according to claim 2 wherein the rotor comprises a first layer of a non-magnetic material or material with negligible magnetic properties and/or a non-ferromagnetic material and a second layer of magnetic or ferromagnetic material, the at least one reference section being integral or being attached to the first layer and the at least one actionable section being integral or being attached to the second layer.

5. Rotor according to claim 1 wherein the rotor is manufactured as one piece made of or comprising a magnetic or ferromagnetic material.

6. Rotor according to claim 1 wherein the at least one actionable section is engageable with a blocking element, when the at least one actionable section is in the rest position, thereby locking and preventing the rotor to rotate, and wherein the at least one actionable section is disengageable from the blocking element by moving the at least one actionable section from the rest position to the stretched position, thereby unlocking and allowing the rotor to rotate.

7. Medical flow-regulating device comprising a rotor according to claim 1.

8. Medical flow-regulating device according to claim 7 further comprising at least one blocking element engageable with the at least one actionable section in the rest position.

9. Medical flow-regulating device according to claim 7 further comprising a pump or a valve directly or indirectly connected or connectable to the rotor for regulating a fluid flow when the rotor is rotated.

10. System comprising a medical flow regulating device according to claim 7 and the hand-held activation device separate from the medical flow-regulating device, the activation device comprising an unlocking/drive unit, wherein in absence of the activation device the rotor is locked and prevented to rotate by engagement of the at least one actionable section in the rest position with the blocking element and wherein the rotor is unlockable and rotatable by temporarily docking the activation device to the medical flow-regulating device in an energy transfer position, which enables the unlocking/drive unit to transfer the force required to move the at least one actionable section to the stretched position thereby unlocking the rotor and to transfer a rotational force to the rotor required for rotating the unlocked rotor and wherein the rotor is again lockable by removing the activation device from the energy-transfer position.

* * * * *